US00PP10110P

United States Patent [19]

Trees

[11] Patent Number: Plant 10,110

[45] Date of Patent: Nov. 4, 1997

[54] NEW GUINEA IMPATIENS NAMED 'BFP-684 SCARLET'

[75] Inventor: Scott C. Trees, Arroyo Grande, Calif.

[73] Assignee: Ball Horticultural Company, West Chicago, Ill.

[21] Appl. No.: 685,672

[22] Filed: Jul. 24, 1996

[51] Int. Cl.[6] ..... A01H 5/00

[52] U.S. Cl. ..... Plt./87.6

[58] Field of Search ..... Plt./87.4

[56] References Cited

PUBLICATIONS

GTITM UPOVROM Listing for CA PBR 96–907 Impatiens 'BFP–684 Scarlet' filed Jul. 5, 1996, Oct. 31, 1996.

*Primary Examiner*—James R. Feyrer

*Attorney, Agent, or Firm*—Burns, Doane, Swecker & Mathis, L.L.P.

[57] ABSTRACT

A new and distinct New Guinea Impatiens cultivar named 'BFP-684 Scarlet' is provided. This new cultivar was the result of a controlled breeding program wherein the 'Tahiti' cultivar (U.S. Plant Pat. No. 8,601) was pollinated by the 'Raspberry Rose' cultivar (U.S. Plant Pat. No. 9,212). The new cultivar forms large scarlet red flowers that display an iridescent appearance. The foliage is medium green in coloration. An attractive compact upright growth habit is exhibited. The new cultivar can be readily distinguished from the 'BSR-181 Bright Scarlet' cultivar (U.S. Plant Pat. No. 8,406).

1 Drawing Sheet

SUMMARY OF THE INVENTION

The present invention comprises a new and distinctive Impatiens plant, botanically known as New Guinea Impatiens, and hereinafter is referred to by the cultivar name 'BFP-684 Scarlet'.

The new cultivar is the product of a planned breeding program. More specifically, the breeding program which resulted in the production of the new cultivar was carried out in a controlled environment during 1993 at Arroyo Grande, Calif., U.S.A. The female parent (i.e., the seed parent) was the 'Tahiti' cultivar (U.S. Plant Pat. No. 8,601) which exhibits light pink blossoms, dark green foliage, and a compact growth habit. The male parent (i.e., the pollen parent) was the 'Raspberry Rose' cultivar (U.S. Plant Pat. No. 9,212) which exhibits rose pink blooms with a white eye, medium green foliage, and a medium growth habit. The parentage of the new cultivar can be summarized as follows:

'Tahiti'×'Raspberry Rose'.

The seeds resulting from the above pollination were sown and plantlets were obtained which were physically and biologically different from each other. Selective study resulted in the identification of a single plant of the new cultivar. This plant initially was designated BFP-684.

It was found that the new cultivar of the present invention:

(a) exhibits attractive large scarlet red flowers,
(b) forms medium green foliage,
(c) exhibits a good basal branching character, and
(d) exhibits a compact upright growth habit.

The new plant exhibits good vigor and is very free-flowering. The scarlet blossoms contrast nicely with the medium green foliage. Plants of the new cultivar can be grown close together in the greenhouse.

Asexual reproduction of the new cultivar by terminal or stem cuttings taken during 1994, at Arroyo Grande, Calif., U.S.A. has demonstrated that the characteristics of the new cultivar as herein described are firmly fixed and are retained through successive generations of such asexual propagation.

The 'BFP-684 Scarlet' cultivar has not been observed under all possible environmental conditions to date. Accordingly, it is possible that the phenotype may vary somewhat with variations in the environment, such as temperature, light intensity, and day length.

When the new cultivar of the present invention is compared to the 'BSR-181 Bright Scarlet' cultivar (U.S. Plant Pat. No. 8,406), it is found that the new cultivar exhibits smaller flowers and a more compact growth habit.

Plants of the new cultivar are marketed under the CELEBRETTE trademark by the Ball Horticultural Company.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is The R.H.S. Colour Chart of The Royal Horticultural Society, London, England. The plants were produced from cuttings taken from stock plants of the new cultivar and were transplanted during early November into 10 cm. (4 inch pots) and were grown in a soilless growth medium under standard greenhouse conditions at West Chicago, Ill., U.S.A. The greenhouse temperature was maintained at approximately 72° F. during the day and approximately 65° F. during the night. The plants were in flower eight to nine weeks later when the observations described hereafter were taken.

Botanical classification: *Impatiens hawkeri.*

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant description:

*Form.*—Basal branching.

*Habit of growth.*—Compact upright mounded Internode lengths of approximately 1.7 to 2.2 cm. commonly are exhibited. A mature plant commonly measures approximately 6 to 7 cm. in height and approximately 15 to 18 cm. in width. This compares to a height of approximately 8 to 9 cm. and a width of approximately 19 to 25 cm. for the 'BSR-181 Bright Scarlet' cultivar.

*Foliage.*—The configuration is elliptic with an acuminate apex and an acuminate base. The mature leaves of the new cultivar measure approximately 7.7 to 9 cm. in length×approximately 3 to 3.1 cm. in maximal width compared to approximately 10 to 12 cm. in length×approximately 2.9 to 3 cm. in maximal width for the 'BSR-181 Bright Scarlet' cultivar. The leaf margins are serrate (as illustrated). The mature foliage of new cultivar is Green Group 139A (adaxial), and Green Group 137C (abaxial) for both the new cultivar and the 'BSR-181 Bright Scarlet' cultivar. The stem coloration is Yellow-Green Group 145C which can be compared to Green Group 135C for the 'BSR-181 Bright Scarlet' cultivar.

Flower description:

*Flowering habit.*—Freely flowering.

*Natural flowering season.*—Throughout the year in a greenhouse environment.

*Flowers borne.*—Above foliage, arising from leaf axils.

*Flower color.*—Lighter and brighter than Red Group 45B with the centers of the lower two petals being Red Group 53C (adaxial), and Red Group 45C (abaxial). This can be compared to Red Group 44B (adaxial) and Red Group 42A (abaxial) for the 'BSR-181 Bright Scarlet' cultivar.

*Quantity of flowers.*—Approximately 3 to 5 per axil which can be compared to approximately 4 to 6 per axil for the 'BSR-181 Bright Scarlet' cultivar.

*Number of petals.*—Five, and overlapping.

*Petal shape.*—Heart-shaped to rounded.

*Flower size.*—Approximately 6 to 5.5 cm. in length and approximately 6.5 to 7 cm. in width. This can be compared to approximately 7 to 7.5 cm. in length and approximately 7 to 7.3 cm. in width for the 'BSR-181 Bright Scarlet' cultivar.

*Flower buds.*—Ellipsoidal in configuration, and generally covered with three sepals plus two rudimentary sepals fused into the under surface of the superior petal. A spur originating from the base of the inferior sepal is approximately 5 to 5.3 cm. in length on fully opened flowers which can be compared to a length of approximately 6.5 to 7.0 cm. for the spur of the 'BSR-181 Bright Scarlet' cultivar. The spur coloration is Red Group 53A which can be compared to Red Group 47A for 'BSR-181 Bright Scarlet' cultivar.

*Reproductive organs.*—The stamens are Red Group 45C at the base and generally are colorless at the outer edge. The anthers tend to be fused together forming one organ that surrounds the pistil. Commonly the anthers shed pollen prior to the stigma becoming receptive. The pollen coloration is Yellow Group 11D, and the ovary coloration is Green Group 141A. This can be compared to a stamen coloration of Red-Purple Group 63A at the base and generally colorless at the outer edge, a pollen coloration of White Group 155D, and an ovary coloration of Yellow-Green Group 144D for the 'BSR-181 Bright Scarlet' cultivar.

I claim:

1. A new and distinct cultivar of New Guinea Impatiens plant named 'BFP-684 Scarlet', substantially as herein shown and described, which:

(a) exhibits attractive large scarlet red flowers,
(b) forms medium green foliage,
(c) exhibits a good basal branching character, and
(d) exhibits a compact upright growth habit.

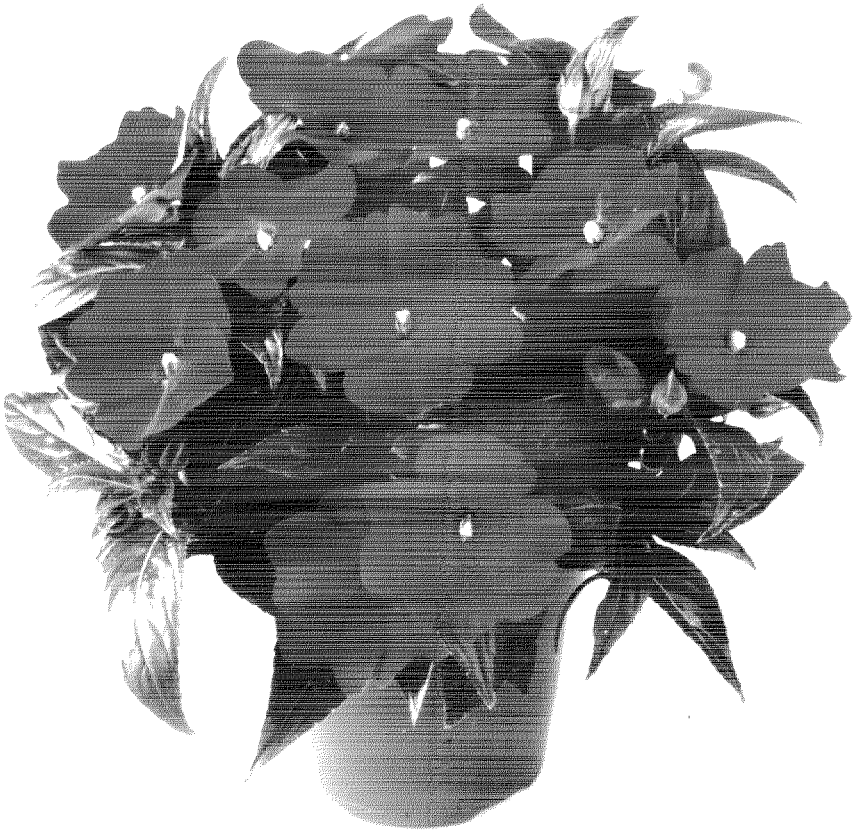

* * * * *